(12) United States Patent
Lang

(10) Patent No.: US 7,517,354 B2
(45) Date of Patent: Apr. 14, 2009

(54) MEDICAL INSTRUMENT

(75) Inventor: Dieter Lang, Stockheim (DE)

(73) Assignee: Karl Storz GmbH & Co. KG (DE)

( * ) Notice: Subject to any disclaimer, the term of this patent is extended or adjusted under 35 U.S.C. 154(b) by 836 days.

(21) Appl. No.: 10/872,846

(22) Filed: Jun. 21, 2004

(65) Prior Publication Data

US 2005/0038469 A1 Feb. 17, 2005

(30) Foreign Application Priority Data

Jun. 20, 2003 (DE) ................. 103 27 655

(51) Int. Cl.
*A61B 17/28* (2006.01)
(52) U.S. Cl. .................................... 606/208
(58) Field of Classification Search ............... 606/170, 606/174, 180, 205–210, 48, 50, 52, 148; 600/227, 234
See application file for complete search history.

(56) References Cited

U.S. PATENT DOCUMENTS

| 4,258,716 A | | 3/1981 | Sutherland ................ 128/318 |
| 5,374,277 A | * | 12/1994 | Hassler ...................... 606/207 |
| 5,383,888 A | * | 1/1995 | Zvenyatsky et al. ......... 606/206 |

FOREIGN PATENT DOCUMENTS

DE     G 83 02 716.5    5/1983

| DE | G 83 11 392.4 | 12/1983 |
| DE | G 84 18 993.2 | 9/1984 |
| DE | G 91 15 760.9 | 3/1992 |
| DE | 94 05 468.1 | 6/1994 |
| EP | 1 250 891 A2 | 10/2002 |

OTHER PUBLICATIONS

European Search Report, Sep. 21, 2004.

* cited by examiner

*Primary Examiner*—Kevin T Truong
(74) *Attorney, Agent, or Firm*—St. Onge Steward Johnston & Reens LLC

(57) ABSTRACT

The invention relates to a medical instrument having a hollow shaft (2) and, positioned on its proximal end, a handle (3) consisting of at least two gripping members (3a, 3b) and, on its distal end, a tool consisting of at least two jaw members (5a, 5b). The instrument's jaw members (5a, 5b) are stationed at a lateral angle to the longitudinal axis of the shaft (2) so that at least one jaw member (5a) of the tool (5) can be moved for opening and closing by means of a gripping member (3b) of the handle (3) that can be rotated with respect to the at least one other jaw member (5b) of the tool (5) and the at least one movable jaw member (5a) and the corresponding gripping member (3b) of the handle (3) serving to move the jaw member (5a) are connected to one another by a compression-tension element (8) positioned in the hollow shaft (2). To ensure that power is transmitted precisely and without free play to the tool, it is proposed with the invention that the compression-tension element (8) and the respective jaw member (5a) of the tool (5) are connected to one another by a transmission lever (7).

8 Claims, 4 Drawing Sheets

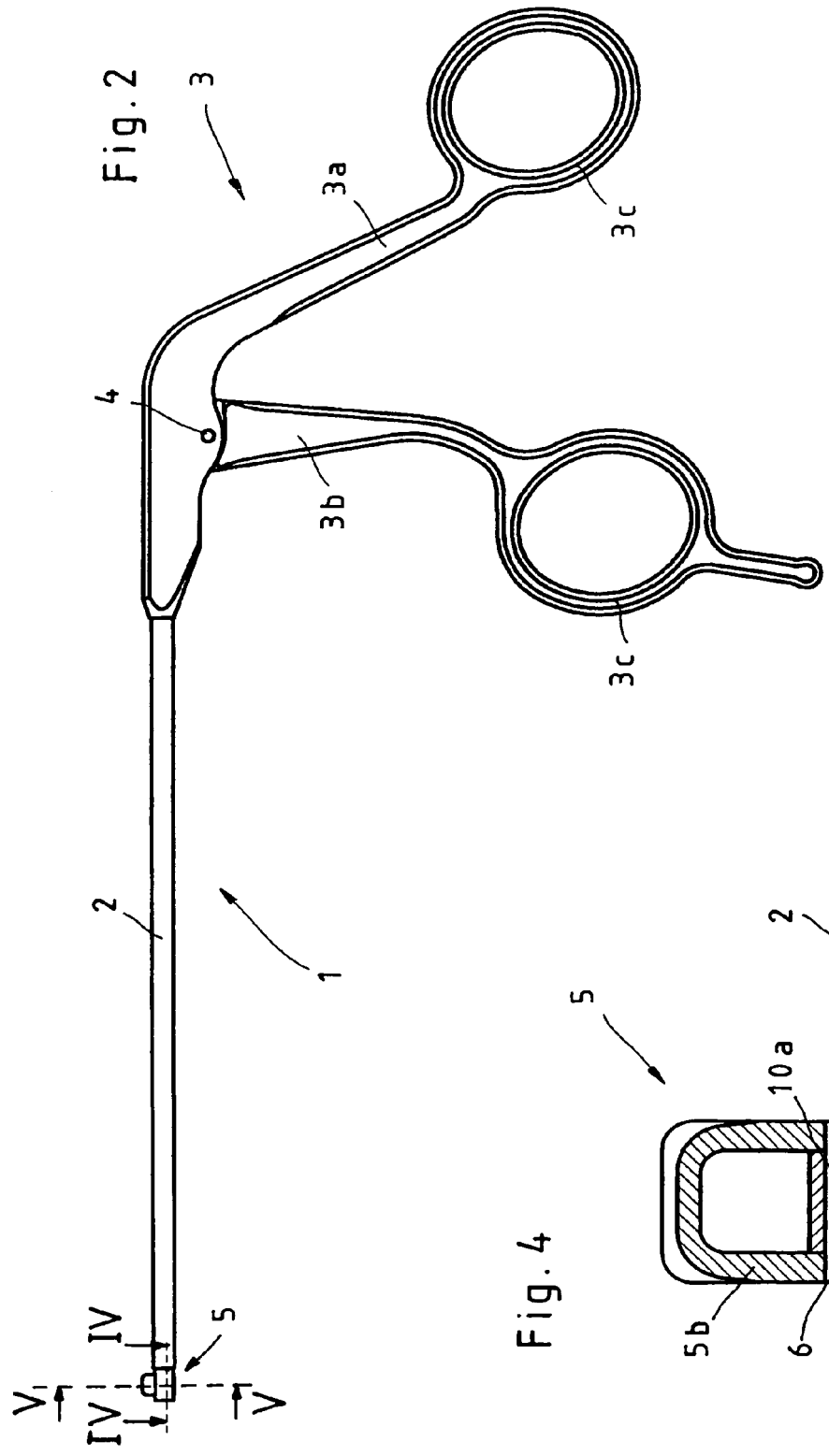

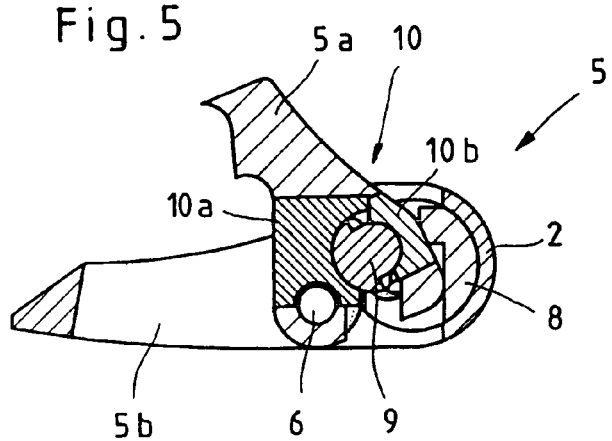
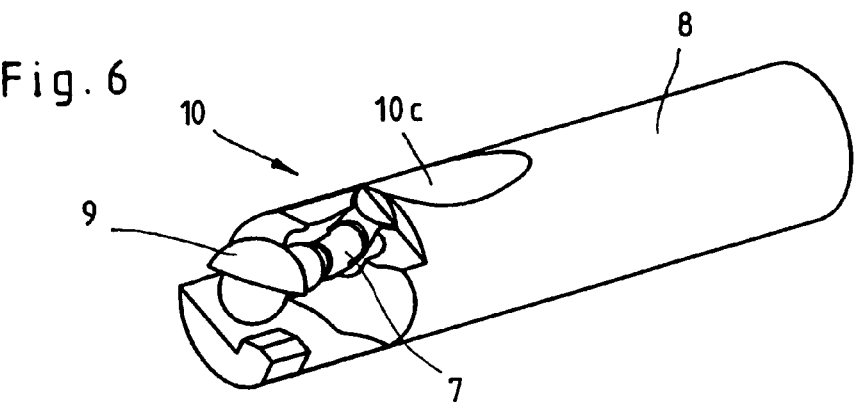
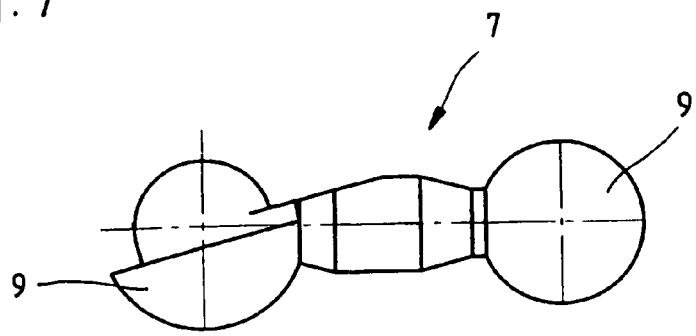

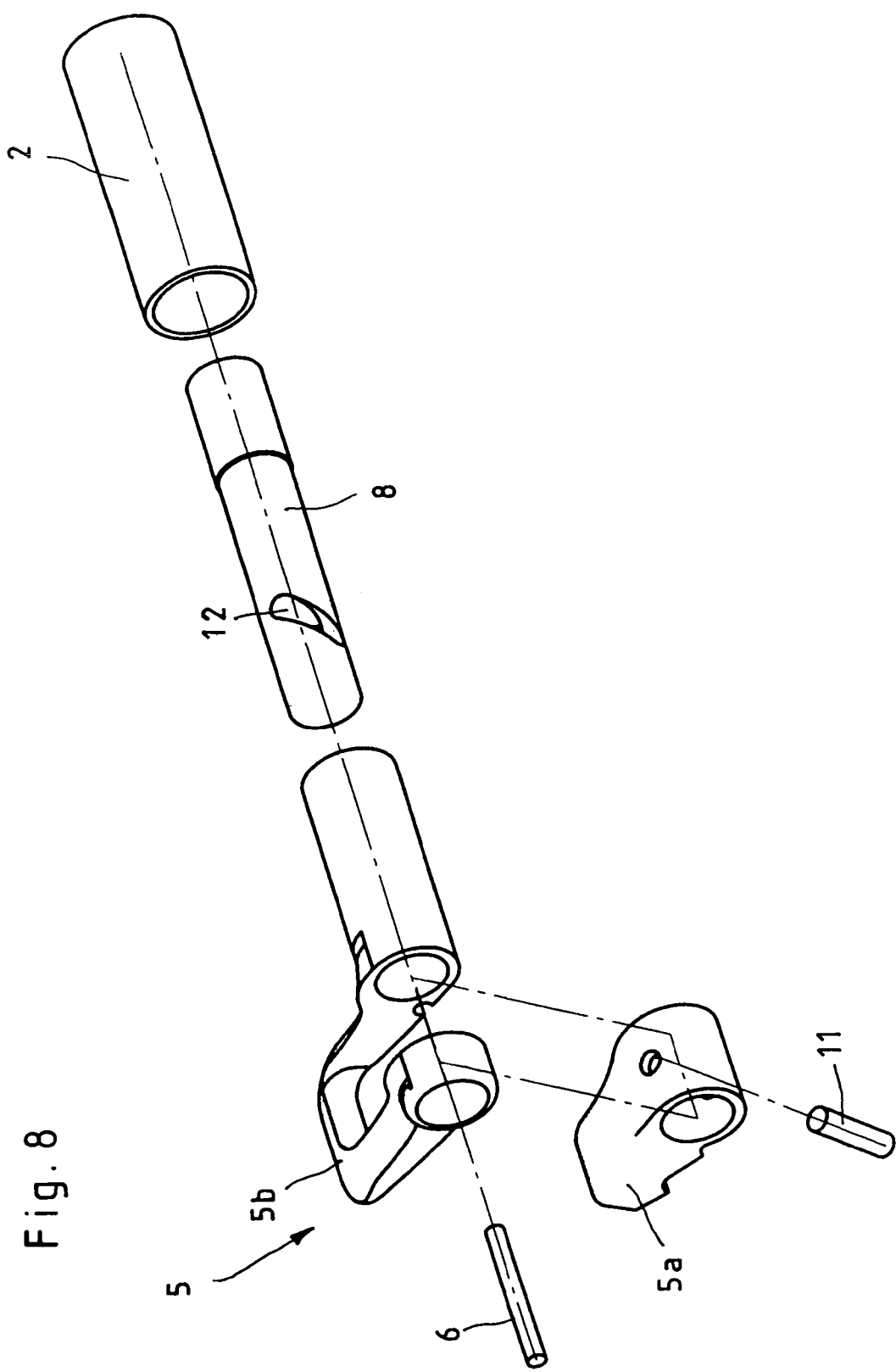

MEDICAL INSTRUMENT

This application claims priority of pending German Patent Application No. 103 27 655.6 filed on Jun. 20, 2003.

FIELD OF THE INVENTION

The invention relates to a medical instrument having a hollow shaft and, positioned on its proximal end, a handle consisting of at least two gripping members and, on its distal end, a tool consisting of at least two jaw members. The instrument's jaw members are stationed at a lateral angle to the longitudinal axis of the shaft so that at least one jaw member of the tool can be moved for opening and closing by means of a gripping member of the handle that can be rotated with respect to the at least one other jaw member of the tool and the at least one movable jaw member and the corresponding gripping member of the handle serving to move the jaw member are connected to one another by a push/pull element positioned in the hollow shaft.

Conventional medical instruments, in which the movable jaw member can be activated by means of a push/pull element starting from a rotatable gripping member of the handle, are widely used especially in endoscopic surgery, for instance as punches, scissors, needle holders, gripping instruments, and the like. In most of the well-known instruments the jaw members that form the tool are arranged in the longitudinal direction of the instrument shaft, so that these instruments serve to reach only operating areas that are situated to be directly accessible, mainly in front of the instrument tip. However, since several operating areas are not accessible in a direct straight line, these familiar instruments are not suited for these purposes, or else can be used only under certain conditions.

To be able to provide secure and precise access to operating areas that are also to the side of the instrument's longitudinal axis, there are also medical instruments in which the tool's jaw members are positioned at a lateral angle to the longitudinal axis of the shaft. An instrument of this kind is presented, for instance, in patent DE 91 14 760 01.

These familiar medical instruments usually involve a medical pincer whose jaw members are configured and positioned so that they open on the end away from the patient. For this purpose the rigid jaw member is designed to be hook-shaped and bent back so that the opening angle between the rigid jaw member and the instrument shaft is directed toward the proximal end of the pincer. The movable jaw member is inserted from above into a slit in the housing of the rigid jaw member so that the connection between the movable jaw member and the activation rod is provided by a disk that can be inserted into a bore hole in this jaw member and the activation rod is suspended in this bore hole.

Both the positioning of the disk in the movable jaw member and the positioning of the movable jaw member in the rigid jaw member housing provide a certain free play that allows the activation rod to move with respect to the movable jaw member together with the disk. This familiar medical pincer has the structural disadvantage that the coupling between the activation rod and the movable jaw member has free play at various storage positions, so that motion of the activation rod by means of the gripping element does not lead immediately, without hesitation, to activation of the movable jaw member. Because of this free play, it is impossible for the operator to activate the pincer in a controlled, calibrated manner, because it is necessary first to overcome the existing play before the pincer can grip.

Consequently, it is the aim of the invention to provide a medical instrument of the aforementioned type in such a way that it can ensure power transmission onto the tool that is precise and without free play.

The invention fulfills this aim in a distinctive manner in that the push/pull element and the respective jaw member of the tool are connected to one another by means of a transmission lever.

Thanks to the invention's coupling of the push/pull element with the jaw member that is to be activated, by means of an interposed transmission lever, power transmission of the force exerted by the handle on the movable jaw member is guaranteed to be free at all times of free play and thus capable of direct transmission of the force exerted by the handle onto the movable jaw member.

Direct power transmission allows the operator to apply force purposefully and in calibrated quantities. Rather than being obliged first to overcome a dead space caused by free play, the activation of the handle now causes an immediate reaction of the jaw member. By means of corresponding design of the particular transmission lever, it is even possible to distribute according to function the forces to be transmitted and thus to provide the operator with an even better cutting and gripping sensation.

To avoid a dead point in power transmission from the push/pull element to the adjustable jaw member, the transmission lever is situated at an angle in the direction toward the tool.

According to a first embodiment of the invention, the transmission lever takes the form of a two-sided rotatably mounted transmission lever, both of whose free ends have spherical joint, which are each positioned in corresponding spherical recesses in the movable jaw member or on the push/pull element.

It is proposed with a preferred embodiment of the invention that the spherical joint positioned on the movable jaw member and/or the spherical joint positioned on the push/pull element consists of two hemispheres with different diameters. Use of the two different-sized hemispheres makes it possible to distribute the forces that are to be transmitted, such as for instance the force for simply opening the jaw member and the cutting, punching, or holding forces that are to be exerted by the jaw member, on the different hemispheres, In addition to the exact sizing of the hemispheric sizes on the forces to be transmitted, this ensures that the operator has a good, precise cutting sensation.

To configure the spherical recesses on the jaw member and on the push/pull element, it is proposed with the invention that these essentially consist of mounting elements that can be inserted into the various components, that is, of one or two mounting elements that can be inserted into the movable jaw member, with one of the mounting elements serving to secure the spherical joint in the recess and the other possible mounting element serving to secure one axis around which the jaw member rotates, as well as of a mounting element that can be inserted into the pull/pull element. The use of these insertable mounting elements has the advantage that the mounting elements and also the transmission lever are easily accessible for purposes of maintenance and repair.

According to a second embodiment of the invention, the transmission lever is configured as a rod that is firmly connected with the push/pull element and engages in a corresponding guide track in the movable jaw member or in a corresponding guide tracks in each movable jaw member.

Alternatively, with a third embodiment of the invention it is proposed that the transmission lever is configured as a rod that is firmly connected with a movable jaw member and engages in a corresponding guide track in the push/pull element.

It is finally proposed with a fourth embodiment of the transmission lever that the transmission lever is configured as a rod that is firmly connected with the push/pull element and on the distal side is positioned in a cylindrical casing which in turn is mounted in a corresponding guide track in a movable jaw member, so that force is transmitted from the rod onto the cylindrical casing and from this casing further onto the jaw member.

Additional characteristics and advantages of the invention are presented with the help of descriptions of the associated illustration, in which two embodiments of an inventive medical instrument are schematically presented.

BRIEF DESCRIPTION OF THE DRAWINGS

FIG. 2 shows a view as in FIG. 1 but with jaw members opened.

FIG. 4 shows an enlarged section along the line IV-IV as in FIG. 2.

FIG. 5 shows an enlarged section along the line V-V as in FIG. 2.

FIG. 6 shows a perspective detail view of the distal end of the push/pull element equipped with a transmission lever.

FIG. 7 shows a lateral view of a transmission lever.

FIG. 8 shows a detail explosion view of a second embodiment of an inventive medical instrument.

DETAILED DESCRIPTION OF DRAWINGS

Figure 1:
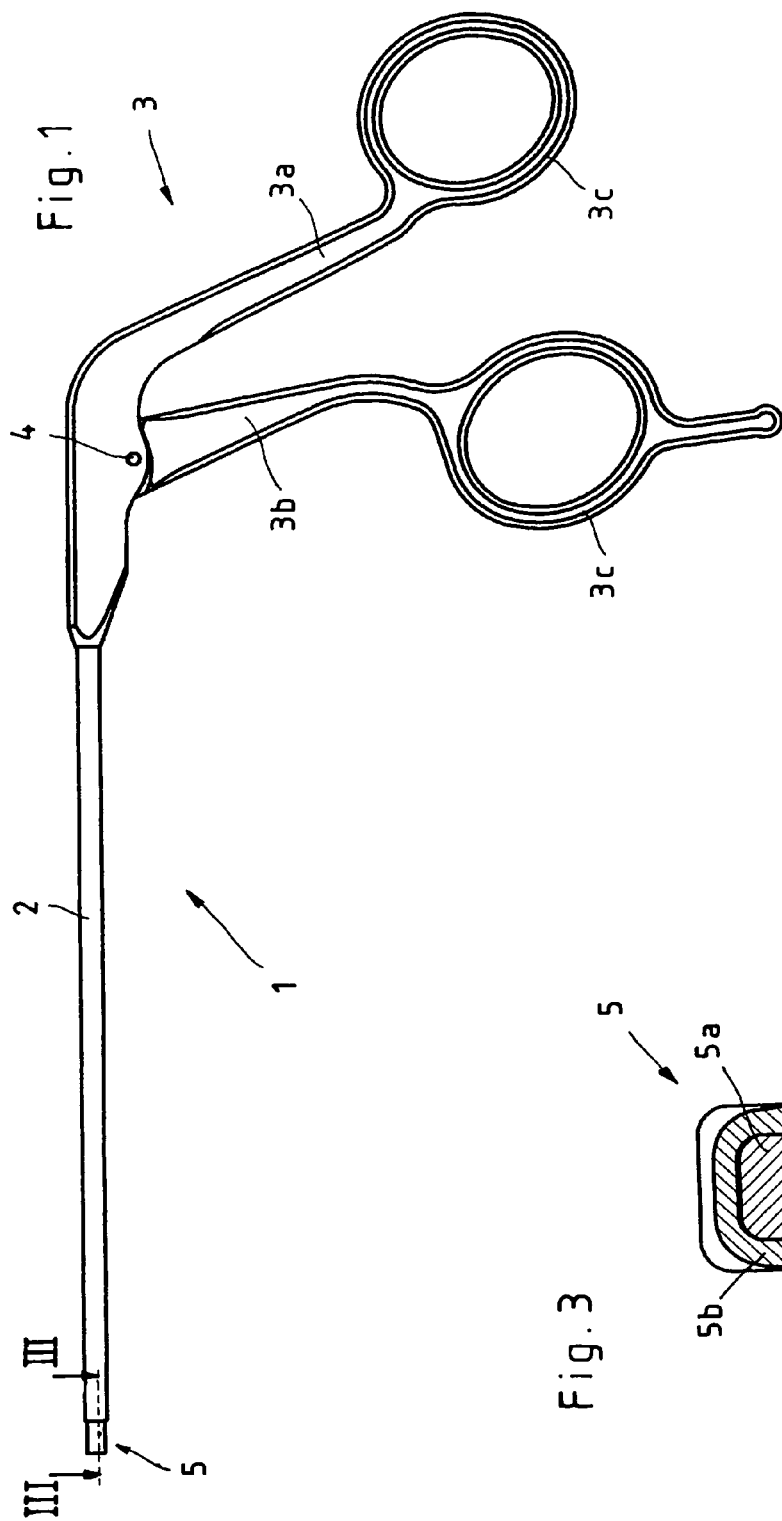
FIG. 1 shows a side view of a first embodiment of an inventive medical instrument, showing the jaw members in the closed position.

FIGS. 1 and 2 present lateral views of a medical instrument 1 whose power transmission mechanism has multiple applications, for instance as punches, scissors, needle holders, grasping instruments, and the like.

The medical instrument 1 consists essentially of a hollow shaft 2 on whose proximal end a handle 3 is mounted consisting of a rigid gripping member 3a and a gripping member 3b that can rotate around a rotation axis 4 with respect to the rigid gripping member 3a. On the distal end of the shaft 2 there is a tool 5, which in the illustrated embodiment (FIG. 5) consists of a rotatable jaw member 5a and a jaw member 5b that is rigidly connected with the shaft 2, in such manner that the rotatable jaw member 5a can rotate with respect to the rigid jaw member 5b around a rotation axis 6.

Figure 3:
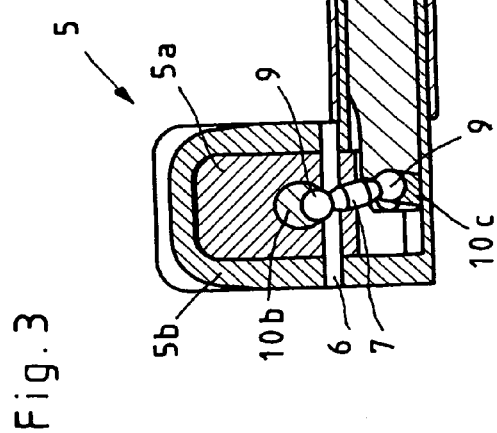
FIG. 3 shows an enlarged section along the line III-III as in FIG. 1.

As can be seen from the sectional depictions in FIGS. 3 and 4, the jaw members 5a, 5b of the tool 5 are configured as bent to the side with respect to the longitudinal axis of the shaft 2. In the embodiments illustrated in FIGS. 3, 4, and 6, the jaw members 5a, 5b are each at a right angle to the longitudinal axis of the instrument shaft. Other angles between zero and 90 degrees and even greater are also workable, however.

Thanks to the angle between the work tool 5 and the shaft 2, it is possible, with a medical instrument 1 configured in this manner, to reach even operating areas that are difficult to get at or inaccessible in a direct, straight-line path.

The sectional depictions in FIGS. 1 and 4 show the particular characteristic of the illustrated medical instrument 1, that is, the connection of the rotatable jaw member 5a by means of a transmission gear 7 with a push/pull element 8, which is mounted in the hollow shaft 2 on the proximal side and connected with the rotatable gripping member 3b of the handle 3 in such manner that the rotatable jaw member 5a can be moved from the closed position (FIGS. 1 and 3) into the opened position (FIGS. 2 and 4) or vice versa by means of the rotation of the gripping member 3b. The push/pull element 8 is advantageously configured as a push/pull rod.

The transmission lever 7 used in this embodiment serves to transform and transmit the transmission movement exerted by the push/pull element 8 in the longitudinal direction of the shaft 2 into the rotation movement of the rotatable jaw member 5a that is mounted at a right angle to the shaft 2. As can be seen in particular from FIG. 7, the transmission lever 7 has spherical joints 9 at both free ends and by means of these spheres the transmission lever 8 is mounted in corresponding spherical recesses 10 on the movable jaw member 5a and on the push/pull element 8.

In the illustrated embodiment of a transmission lever 7, the spherical joint 9 on the distal side, which is mounted on the rotatable jaw member 5a, is configured to consist of two hemispheres, in such manner that each hemisphere has a different diameter. In this arrangement, the hemisphere with the smaller diameter serves predominantly to exert the punching or cutting force of the movable jaw member 5a, while the hemisphere with the greater diameter serves primarily to transmit the forces exerted by the push/pull element 8 to open the tool 5. Thanks to the variation in hemisphere diameter, it is possible to enlarge the distance between the two hemispheres' center points, while the distance between the proximal end and the distal end of the transmission lever 7 remains essentially unchanged, and this in turn has an impact on the mental leverage ratios (for simplification of computation) and consequently on the forces to be transmitted. Even the actual lever arm, configured by the transmission lever 7 (that is, the distance between the proximal end and the distal end of the transmission lever 7), can be increased or diminished by varying the diameter of the hemispheres of the proximal and distal spherical joints 9.

The configuration of the smaller hemisphere to exert the punching or cutting forces also has the advantage that it better protects the power-exerting larger hemisphere from coming out of the spherical recess 10 by withdrawing the push/pull element 8, opening the jaw member 5a.

In addition to the illustrated embodiment with the spherical joint 9 made up of different-sized hemispheres on the distal end of the transmission lever 8, it is also possible of course, alternatively or in addition, to form the proximal-side spherical joint 9 mounted on the push/pull element 8 from two different-sized hemispheres. There is also the possibility to form the hemisphere that exerts the punching or cutting forces as the hemisphere with the greater diameter. In this configuration the lever arm of the entire transmission lever 7, that is, the distance between the distal sphere border of the distal spherical joint 9 and the proximal sphere border of the proximal spherical joint 9, can be increased so that the material strength of the spherical recesses 10 can be reduced with declining hemispherical diameter.

To allow simple installation of the transmission lever 7, the spherical recesses 10 for storing the spherical joint 9 are configured as mounting elements 10a, 10b, and 10c that can be inserted into the movable jaw member 5a and the push/pull element 8. In the embodiment illustrated in FIGS. 5 and 6 there are two mounting elements 10a and 10b on the movable jaw member 5a and one mounting element 10c on the push/pull element 8.

FIG. 8 shows an alternative embodiment to the conformation of the transmission lever 7 for coupling of the push/pull element 8 with the rotatable jaw member 5a. According to this alternative embodiment the transmission lever is configured as a rod 11 securely connected with the movable jaw member 5a, and this rod 11 engages in a corresponding guide track 12 in the push/pull element 8. When there is a movement of the push/pull element 8 in the longitudinal direction, the rod 11, which is positioned perpendicular to the longitudinal direction of the shaft 2, moves in the guide track 12, which is shaped in such manner that it is arched, so that the rotatable jaw member 5a can be opened and closed by means of the rod 11 running in the guide track 12. The transmission of moving force/jaw member force (punching or cutting forces) can be adjusted in this embodiment by corresponding adjusting of the track curve of the guide track 12 so that the transmission is either constant over the entire track curve or else can be variably adjusted.

The medical instrument 1 illustrated in figs. 1 to 7 is activated as follows:

To ensure secure gripping of the gripping members 3a, 3b of the handle 3, they have finger loops 3c on their free ends. By rotation of the gripping member 3b around the rotation axis 4, the push/pull element 8 coupled with this gripping member 3b is moved in the longitudinal direction of the shaft 2. To transmit this translational movement of the push/pull element 8 onto the rotatable jaw member 5a, the push/pull element 8 and the movable jaw member 5a are coupled together in the illustrated embodiment by means of the transmission lever 7. To avoid a dead position that would block this motion, the transmission lever 7, as shown in FIGS. 3 and 4, is positioned bent at an angle in the direction toward the tool 5.

Alternatively to the illustrated embodiment, it is also possible to position the transmission lever 7 in such a way that it runs essentially in the opposite direction to the push/pull element 8, that is, it is bent toward the proximal end, which is especially appropriate for tools 5 that are likewise bent in proximal direction. In this embodiment, in which the jaw members 5a, 5b of the tool 5 are bent at an angle to the proximal end of the medical instrument 1 heading toward the instrument longitudinal axis, the bending of the transmission lever 7 causes the tool 5 to open upon closing of the gripping members 3a, 3b of the handle 3, that is, works contrary to the usual method of operation.

The medical instrument 1 illustrated in FIGS. 1 to 7 is activated as follows:

By moving the point of the push/pull element 8 on the rotatable gripping member 3b from the side toward the operator's hand with respect to the rotation axis 4 to the side turned toward the operator's hand, or vice versa, even with a transmission lever 7 turned, away from the tool 5, the activation of the tool 5 can again be adjusted in such a way that the closing of the gripping members 3a, 3b of the handle 3 cause the tool 5 to close.

It is thus possible, by means of the push/pull element 8 and the transmission lever 7, to move the tool 5, which is positioned at a right angle to the longitudinal axis of the instrument shaft, by activating the rotatable handgrip 3b between a closed position of the jaw members 5a, 5b (FIGS. 1 and 3) and an opened position of the jaw members 5a, 5b (FIGS. 2 and 4).

| Illustration Key | |
|---|---|
| 1 | Medical instrument |
| 2 | Shaft |
| 3 | Handle |
| 3a | Rigid gripping member |
| 3b | Rotatable gripping member |
| 3c | Finger loop |
| 4 | Axis of rotation |
| 5 | Tool |
| 5a | Rotatable jaw member |
| 5b | Rigid jaw member |
| 6 | Axis of rotation |
| 7 | Transmission lever |
| 8 | Compression-tension element |

-continued

| Illustration Key | |
|---|---|
| 9 | Link bearing |
| 10 | Spherical recess |
| 10a | Mounting element |
| 10b | Mounting element |
| 10c | Mounting element |
| 11 | Rod |
| 12 | Guide track |

What is claimed is:

1. A medical instrument having a hollow shaft and, positioned on its proximal end, a handle consisting of at least two gripping members and, on its distal end, a tool consisting of at least two jaw members;

the instrument's jaw members being stationed at a lateral angle to the longitudinal axis of the shaft so that at least one jaw member of the tool can be moved for opening and closing by means of a gripping member of the handle the can be rotated with respect to the at least one other jaw member of the tool and the at least one movable jaw member and the corresponding gripping member of the handle serving to move the jaw member are connected to one another by a push/pull element positioned in the hollow shaft wherein the push/pull element and the respective jaw member of the tool are connected to one another by a transmission lever;

wherein said transmission lever includes a spherical joint at each end of said transmission lever;

wherein the transmission lever is positioned at an angle in the direction toward the tool;

wherein the transmission lever is configured as a transmission lever mounted so that it can be rotated to both sides; and wherein the transmission lever has spherical joints on both free ends which are each mounted in corresponding spherical recesses on the movable jaw member and on the push/pull element.

2. Medical instrument as in claim 1, wherein the spherical joint mounted on the movable jaw member and/or the spherical joint mounted on the push/pull element includes two hemispheres with different diameters.

3. Medical instrument as in claim 2, wherein the bearing recess on the movable jaw member consists of one or two mounting elements that can be inserted into the jaw member.

4. Medical instrument as in claim 3, wherein the bearing recess on the push/pull element has a mounting element that can be inserted into the push/pull element.

5. Medical instrument as in claim 1, wherein the transmission lever is configured as a rod that is firmly connected firmly with the push/pull element and that engages with corresponding guide tracks in each movable jaw member.

6. Medical instrument as in claim 1, wherein the transmission lever is configured as a rod that is firmly connected with the jaw member and that engages in a corresponding guide track in the push/pull element.

7. Medical instrument as in claim 1, wherein the transmission lever is configured as a rod that is firmly connected with the push/pull element and that is mounted on the distal side in a cylindrical casing that in turn is mounted in a corresponding guide track in a movable jaw member.

8. Medical instrument as in claim 7, wherein the push/pull element is configured as a push/pull rod.

* * * * *